(12) United States Patent
Curtis et al.

(10) Patent No.: US 9,067,880 B2
(45) Date of Patent: Jun. 30, 2015

(54) PROCESS FOR PRODUCING METHYL METHACRYLATE HAVING REDUCED BIACETYL CONTENT

(75) Inventors: Michael A. Curtis, Houston, TX (US); David A. Flosser, Missouri City, TX (US); Jamie J. Juliette, Houston, TX (US); Philippe P. Maillot, Kingwood, TX (US); Donna Williams, Pearland, TX (US)

(73) Assignee: Rohm and Haas Company

( * ) Notice: Subject to any disclaimer, the term of this patent is extended or adjusted under 35 U.S.C. 154(b) by 45 days.

(21) Appl. No.: 13/881,498

(22) PCT Filed: Oct. 13, 2011

(86) PCT No.: PCT/US2011/056141
§ 371 (c)(1),
(2), (4) Date: Apr. 25, 2013

(87) PCT Pub. No.: WO2012/060990
PCT Pub. Date: May 10, 2012

(65) Prior Publication Data
US 2013/0217914 A1    Aug. 22, 2013

Related U.S. Application Data

(60) Provisional application No. 61/456,308, filed on Nov. 4, 2010.

(51) Int. Cl.
*C07C 67/48* (2006.01)
*C07C 67/60* (2006.01)

(52) U.S. Cl.
CPC ............... *C07C 67/48* (2013.01); *C07C 67/60* (2013.01)

(58) Field of Classification Search
CPC .............................. C07C 67/48; C07C 67/60
USPC ........................................................ 560/218
See application file for complete search history.

(56) References Cited

U.S. PATENT DOCUMENTS

| | | |
|---|---|---|
| 3,124,609 A | 3/1964 | Higdon |
| 4,668,818 A | 5/1987 | Lipp et al. |
| 5,468,899 A | 11/1995 | Bauer, Jr. et al. |
| 5,585,514 A | 12/1996 | Croizy et al. |

FOREIGN PATENT DOCUMENTS

EP      561264      8/1996

OTHER PUBLICATIONS

Ojovan, Michael I. (2011). Handbook of Advanced Radioactive Waste Conditioning Technologies. Woodhead Publishing, p. 189.*
Haley et al., Organic Reactions in Aqueous Solution at Room Temperature. Part I. The Influence of pH on Condensations involving the Linking of Carbon to Nitrogen and of Carbon to Carbon, J. Chem. Soc., 3155-3174, 1951.*
Daintith, John Martin, Elizabeth (2010). Dictionary of Science (6th Edition). Oxford University Press.p. 530.*
Handbook of Chemistry and Physics Web Edition: Dissociation Constants of Organic Acids, p. 5-94.*
Piletska et al., "Design of molecular imprinted polymers compatible with aqueous environment," Analytica Chimica Acta, 607, 54-60, 2008.*
Ojovan, Michael I. Handbook of Advanced Radioactive Waste Conditioning Technologies. Woodhead Publishing, p. 189 (2011).*
Haley et al., "Organic Reactions in Aqueous Solution at Toom Temperature. Part I. The influence of pH on COndensations involving the Linking of Carbon to Nitrogen and of Carbon to Carbon," J. Chem. Soc., 3155-3174, 1951.*
Daintith, John Martin, Elizabeth, Dictionary of Science ($6^{th}$ Edition). Oxford University Press. p. 530, (2010).*
Paabo et al., "Buffer Solutions of Potassium Dihydrogen Phosphate and Sodium Succinate at 25 degrees C," Journal of Research of the National Bureau of Standards-A, Physics and Chemistry vol. 67A, No. 6, 573-576, 1963.*
Handbook of Chemistry and Physics Web Edition: Dissociation Constants of Organic Acids, p. 5-94, (2014).*
Piletska et al., "Design of molecular imprinted polymers compatible with aqueous environment," ANalytica Chimica Acta, 607, 54-60, (2008).*
"Inorganicly Reinforced Polymide", JP 53-108151 Patent Abstract, Sep. 20, 1978.

* cited by examiner

*Primary Examiner* — Paul A Zucker
*Assistant Examiner* — Mark Luderer

(57) ABSTRACT

This invention provides a process for reducing biacetyl in alpha-, beta-unsaturated carboxylic acid esters, particularly in acrylic or methacrylic (hereinafter "(meth)acrylic") esters, which comprise low levels of weak acid.

9 Claims, No Drawings

PROCESS FOR PRODUCING METHYL METHACRYLATE HAVING REDUCED BIACETYL CONTENT

CROSS-REFERENCE TO RELATED APPLICATIONS

This application claims priority from provisional application Ser. No. 61/456,308, filed Nov. 4, 2010, which is incorporated herein by reference in its entirety.

FIELD OF THE INVENTION

This invention relates to a process for reducing carbonyl-containing impurities in alpha-, beta-unsaturated carboxylic acid esters, particularly in acrylic or methacrylic (hereinafter "(meth)acrylic") esters.

BACKGROUND OF THE INVENTION

Various processes are known for producing alpha-, beta-unsaturated carboxylic acid esters. Some such processes incorporate oxidative steps, such as the vapor phase oxidation of propylene, isobutylene, tertiary butanol, methacrolein, acrolein, or isobutyraldehyde to afford acrylic or methacrylic acid followed by esterification to its respective (meth)acrylic ester. Others involve reaction of acetone cyanohydrin with sulphuric acid to form methacrylamide, which is then esterified with methanol to produce methyl methacrylate. Many, if not all, such processes are known to result in product mixtures which contain quantities of carbonyl-containing impurities such as aldehydes and ketones, for example, without limitation, benzaldehyde, biacetyl, furfural, protoanemonin, methacrolein, and acrolein. These impurities are undesirable because they may react with the alpha-, beta-unsaturated esters in subsequent reactions, they may interact with other reactants which are intended to react with the esters in subsequent reactions, they may react to form colored impurities, or they may directly inhibit subsequent reactions.

In particular, certain end users of methyl methacrylate (MMA) require biacetyl (2,3-butanedione) levels below 3.0 ppm by weight (wppm) to avoid yellowing in poly(methyl methacrylate) sheets. Furthermore, some uses of MMA require biacetyl levels to be below detectable limits. Thus, methods have been developed to reduce biacetyl levels during methyl methacrylate production. A preferred methodology for doing this utilizes ortho-phenylenediamine (oPD) as an additive for complexing with the biacetyl and forming a heavy component that boils much higher than MMA. Prior art (U.S. Pat. No. 4,668,818 and European Patent No. EP 0206230) describes the preferential addition of at least a 20-fold or greater molar excess of oPD relative to biacetyl. In the prior art, oPD is added to the MMA esterification reactor in the presence of a strong acid such as sulfuric acid. The use of amines for removal of carbonyl impurities such as aldehydes and ketones from alpha-, beta-unsaturated acids, such as (meth)acrylic acid, is known. Unfortunately, amines effective for reducing impurities from alpha-, beta-unsaturated acids are not necessarily effective for reducing or removing impurities from alpha-, beta-unsaturated esters. For example, aniline is highly effective in reducing carbonyl impurities from acrylic acid but has been found to be quite ineffective in reducing impurities in butyl acrylate. One reference, Japanese Kokai No. 52-23017 ("JK017"), discloses a process for purifying (meth)acrylic acids and esters by distilling in the presence of polyamines of type $R^1$—NH—R—NH—$R^2$. This method requires the use of neutral conditions and, when "R" is a phenylenic group, the method is effective only when the amino groups are immediately adjacent one to the other (i.e. in the 1, 2, or ortho position). Ortho adjacency is required in the JK017 disclosure because, as taught, the cyclic compound formed between the diamine and a carbonyl impurity cannot result from diaminophenylenes other than from those having the 1,2 relationship. Accordingly, meta- and para-phenylene diamines, for example, are specifically excluded, although it would be advantageous to use diamines such as these because of their low cost and availability.

U.S. Pat. No. 3,124,609 discloses the use of amines such as hydroxylamine and ortho-phenylenediamine for the removal of biacetyl from the MMA esterification reactor mix (i.e., the crude MMA product). The molar ratio of oPD:biacetyl used in the process described in U.S. Pat. No. 3,124,609 was 16:1, followed by a holding period of at least 30 minutes and neutralization of the acid.

U.S. Pat. No. 5,468,899 describes the use of amines including phenylenediamines, but not ortho-phenylenediamine, to remove carbonyl impurities from MMA. While biacetyl removal is not specifically addressed in U.S. Pat. No. 5,468,899, the process requires a neutralization step, and the process requires a holding step with a contact time of several hours prior to further distillation.

Another process is disclosed in U.S. Pat. No. 5,585,514 wherein non-aromatic diamines are added at the product column, during purification of the crude MMA, at a preferred diamine:biacetyl mole ratio of at least 10:1, in the presence of 1-2% methacrylic acid. This process requires a holding period of at least 10 minutes.

In a more recent publication in August 2009, a process has been disclosed wherein up to a 10-fold excess of ortho-phenylenediamine, based on biacetyl content, was added to crude methyl methacrylate prior to the first separations to purify the methyl methacrylate product. See Research Disclosure Database Number 544006, *Research Disclosure Journal*, August 2009.

The problem addressed by the present invention is the reduction of biacetyl from alpha-, beta-unsaturated esters, particularly (meth)acrylic esters, to provide high purity alpha-, beta-unsaturated esters in an efficient and low cost process.

SUMMARY OF THE INVENTION

The present invention provides a process for removing biacetyl from an alpha-, beta-unsaturated carboxylic acid ester. More particularly, the process of the present invention comprises: a) treating a crude alpha-, beta-unsaturated carboxylic acid ester to produce said alpha-, beta-unsaturated carboxylic acid ester which comprises biacetyl and has a weak acid content of between 0.001% and 5.0% by weight, based on the total weight of said alpha-, beta-unsaturated carboxylic acid ester; and b) adding to said alpha-, beta-unsaturated carboxylic acid ester from 1 to 10 molar ratio of an aromatic ortho-diamine, based upon moles of biacetyl, to produce an amine-treated ester mixture. The aromatic ortho-diamine has the formula:

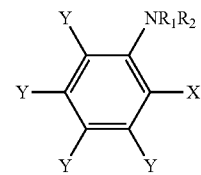

where X is $NR_3R_4$ and $R_1$, $R_2$, $R_3$, $R_4$, and Y are independently selected from hydrogen, alkyl, phenyl, and naphthyl. For example, the aromatic ortho-diamine may be ortho-phenylenediamine The crude alpha-, beta-unsaturated carboxylic acid ester, may be the product of a $C_3$-$C_{10}$ alpha-, beta-unsaturated carboxylic acid and $C_1$-$C_{10}$ alcohol or the product of methacrylamide, which is esterified with a $C_1$-$C_{10}$ alcohol.

The treating step a) may be accomplished by performing one or more separation steps. Additionally, treating step a) may, either independently or along with one or more separation steps, comprise adding a quantity of weak acid to said alpha-, beta-unsaturated carboxylic acid ester sufficient to bring said methacrylic acid content to between 0.001% and 5.0% by weight.

The weak acid content of the alpha-, beta-unsaturated carboxylic acid ester may be between 0.005% and 1% by weight, based on the total weight of the alpha-, beta-unsaturated carboxylic acid ester, such as for example, without limitation, between 0.3% and 0.5% by weight, based on the total weight of said alpha-, beta-unsaturated carboxylic acid ester.

In one embodiment, the weak acid is selected from the group consisting of acrylic acid and methacrylic acid.

The process of the present invention may further comprise separating a diamine-biacetyl adduct and excess oPD from the amine-treated ester mixture to produce a purified alpha-, beta-unsaturated carboxylic acid ester.

DETAILED DESCRIPTION OF THE INVENTION

Alpha-, beta-unsaturated carboxylic acid esters (hereafter "esters") which can be purified using this invention include those produced from the $C_3$-$C_{10}$ alpha-, beta-unsaturated carboxylic acids (for example, acrylic, methacrylic, 2-butenoic, cyclohexenoic, maleic, or itaconic acid), or $C_3$-$C_{10}$ amides (for example, acrylamide or methacrylamide), and the $C_1$-$C_{10}$ alcohols (for example, methanol, ethanol, normal and isopropanol, the butyl alcohols, for example, normal, iso-, sec-, and tert-butanols; cyclohexanol, octanol, ethyl hexanol, glycols, and decanol). The present invention is particularly useful for purifying esters including, but not limited to, for example, methyl acrylate, ethyl acrylate, butyl acrylate, methyl methacrylate and butyl methacrylate. While the following detailed description of the present invention focuses on removal of biacetyl from methyl methacrylate, it will be readily apparent to persons of ordinary skill in the relevant art that the process of the present invention is applicable to removal of biacetyl and other carbonyl-containing impurities from the aforementioned categories of alpha-, beta-unsaturated carboxylic acid esters.

It has been discovered that carbonyl-containing impurities, such as biacetyl, can be substantially reduced or completely removed from alpha-, beta-unsaturated carboxylic acid esters, for example (meth)acrylic esters, by treatment of the ester with one or more aromatic diamines, such as ortho-phenylenediamine, in the presence of a weak acid, which may be organic or inorganic. The treated ester mixture optionally may be subjected to an acid neutralization step with aqueous base, water washing, and distillation. Thus, the present invention provides a new, low cost, simple and effective method for purifying alpha-, beta-unsaturated esters. More particularly, the present invention provides a process for removing biacetyl from an alpha-, beta-unsaturated carboxylic acid ester. Initially, a crude alpha-, beta-unsaturated carboxylic acid ester, which is the product of a $C_3$-$C_{10}$ alpha-, beta-unsaturated carboxylic acid and $C_1$-$C_{10}$ alcohol or the product of methacrylamide, which is esterified with a $C_1$-$C_{10}$ alcohol is treated to produce a alpha-, beta-unsaturated carboxylic acid ester which comprises biacetyl and has a weak acid content of between 0.001% and 5.0% by weight, based on the total weight of the alpha-, beta-unsaturated carboxylic acid ester. To this ester is added from 1 to 10 molar ratio of an aromatic ortho-diamine, based upon moles of biacetyl. The molar ratio of aromatic ortho-diamine added to the ester, based upon moles of biacetyl, may be as high as 10,000, but more than 10 molar ratio is likely inefficient and wasteful. For example, without limitation, a suitable and efficient molar ratio of aromatic ortho-diamine to biacetyl would be between about 1.9:1 and 3:1.

Aromatic ortho-diamines suitable for use in the process of the present invention have the following formula:

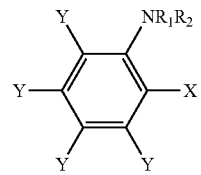

where X is $NR_3R_4$, and $R_1$, $R_2$, $R_3$, $R_4$, and Y are independently selected from hydrogen, alkyl, phenyl and naphthyl, to produce an amine-treated ester mixture. For example, $C_1$-$C_4$ alkyl groups may be advantageously used in the substituted positions of the aromatic ortho-diamines, such as, for example, methyl, ethyl, n- and iso-propyl, and n-, sec-, and iso-butyl groups. The aromatic ortho-diamine may be, for example, ortho-phenylenediamine (oPD).

The time required for complete reaction of the biacetyl with the aromatic ortho-diamine is typically not more than about 10 minutes, for example, between less than 1 minute and 60 minutes, or more particularly, between 0.1 and 5 minutes.

A weak acid, as used herein, means an acid that does not ionize fully when dissolved in water and has an add dissociation constant (on a logarithmic scale), pKa, from −2 to 12, in solution with water at 20° C. For example, methacrylic acid is a weak organic acid and has a pKa of 4.66 at 20° C. in water. Acetic acid is of similar strength, with a pKa of 4.756. Phenol, by comparison, has a pKa of 10 and is a much weaker add than methacrylic or acetic acid.

The weak acid may be an organic or an inorganic acid. Inorganic acids suitable for use in the process of the present invention include, without limitation, hydrogen sulfide, nitric acid and hydrofluoric acid. Organic acids suitable for use in the process of the present invention include carboxylic acids, oxalic acid, methanoic acid, and benzoic acid. Carboxylic acids including, without limitation, acrylic acid, methacrylic acid, formic acid and acetic acid may be advantageously used in the present invention.

The treating step may be accomplished by performing one or more purification steps as are well known and routinely practiced by persons of ordinary skill in the relevant art, such as subjecting the crude alpha-, beta-unsaturated carboxylic acid ester to separations by distillation, stripping, rectification, etc. In some cases, the resulting alpha-, beta-unsaturated carboxylic acid ester product will already contain a small amount of a weak acid. For example, where methacrylic acid is esterified with methanol and the crude methyl methacrylate product is subsequently subjected to distillation or other typically employed purification steps, the resulting methyl methacrylate product will typically comprise small amounts of methacrylic acid, such as between 0.001% and 5.0% by weight methacrylic acid, based on the total weight of the methyl methacrylate product. When the resulting methyl methacrylate product (or other alpha-, beta-unsaturated carboxylic acid ester) comprises less than about 0.001 wt % weak acid, a weak acid may be added to the ester product in a quantity sufficient to bring the weak acid content of the ester product to between 0.001% and 5.0% by weight, for example between 0.25% and 1% by weight, or even between 0.3% and 0.5% by weight, based on the total weight of the ester.

The ester may be treated neat or in solution, i.e., dissolved in a water insoluble organic solvent such as an aromatic solvent such as, for example, without limitation, benzene, toluene, xylenes, or ethyl benzene, and hydrocarbon solvents such as n-hexane, n-heptane, or cyclohexane. Treatment of neat ester and avoidance of solvents is beneficial, however, where a solvent is used, preferred solvents include benzene, toluene, and xylene.

The presence of one or more polymerization inhibitor, for example, hydroquinone (HQ), monomethyl ether of HQ, methylene blue, phenothiazine, copper salicylate, or copper dialkyldithiocarbamates does not adversely affect the process.

The process of the present invention may suitably be performed at temperatures in a range of from about 20° C. to no greater than the normal boiling point of the ester and, in any case, should be less than 150° C. For example, without limitation, a suitable operating temperature would be from 40° C. to 120° C., depending on the ester and not exceeding its normal boiling point. More particularly, the operating temperature may be maintained in the range of 60° C. to 90° C. wherein aromatic ortho-diamine reaction rates with carbonyl compounds, such as biacetyl, are efficient and ester decomposition and by-product formation rates are not high.

In the process of the present invention, in the presence of the weak acid, the aromatic ortho-diamine is believed to complex and form condensation products with biacetyl in the esters. The condensation products may precipitate from solution, thereby facilitating physical separation from the ester. The treated ester may also be distillated to remove the diamine-biacetyl complexes and excess weak acid, thereby producing a highly purified alpha-, beta-unsaturated carboxylic acid ester which is substantially free of biacetyl impurity.

Contrary to known processes wherein stronger acids have been utilized to remove carbonyl-containing impurities, there is no need, and very little benefit to be gained, by neutralizing excess weak acid with an aqueous solution of a base (e.g., sodium carbonate, magnesium carbonate, sodium hydroxide, etc.). Furthermore, the need to "hold" the treated ester for a period of time, typically greater than 10 minutes, at elevated temperatures is also eliminated by the process of the present invention, since the aromatic ortho-diamine is added, in the presence of a weak acid, and reacts with the biacetyl very quickly by comparison. Thus, compared to previously existing methods for removing biacetyl and other carbonyl-containing impurities, at least two process steps are eliminated, so that the process of the present invention is simplified and less costly.

The following examples demonstrate the process of the present invention.

EXAMPLES

Chemicals—the Following Chemicals were Used to Perform the Following Examples

Ortho-phenylenediamine (oPD), biacetyl, and methacrylic acid (MAA) were obtained from Aldrich Chemical Company and used as received. Stripped crude MMA (SCMMA) was obtained from a storage tank at applicants' Deer Park, Tex., USA facility on Mar. 6, 2009. Uninhibited distilled methyl methacrylate (DMMA) was obtained from a tank at the same facility on Apr. 6, 2009, and kept refrigerated until use.

Analytical Method

GC samples were run on an Agilent 7890A with a DB-1 column (60 m×0.250 mm×0.50 μm) with an injector temperature of 200° C. and a detector temperature of 250° C. Calibrations were done via external standards. The oven temperature profile is detailed below:
Start: 40° C.
Program: 10° C./min to 70° C.
Hold 1 minute at 70° C.
Program: 50° C./min to 275° C.
Hold 19 minutes at 275° C.

Comparative Example 1

Biacetyl Removal from DMMA Containing no Methacrylic Acid

Stock Solution A, consisting of 100 wppm biacetyl in uninhibited, MAA-free DMMA, was prepared and the concentration verified by GC using the instrument and methodology described above. Stock solution B, consisting of 1480 wppm oPD in uninhibited, MAA-free DMMA, also was prepared. Stock Solution B was added to Stock Solution A, such that the oPD concentration was 254 wppm, the biacetyl concentration was 82.8 wppm, and the oPD:biacetyl mole ratio was 2.44. After stirring for 5 minutes in a closed system at ambient temperature, the biacetyl concentration was determined to be 65 wppm by GC. After stirring for 60 additional minutes in the closed system at ambient temperature, the biacetyl concentration was determined to be 35 wppm. The solution was stirred overnight in the closed system at ambient temperature and the biacetyl concentration found to be below the GC detection limit. All data can be seen in Table 1 below.

TABLE 1

| Biacetyl Removal from DMMA Containing No Methacrylic Acid | |
|---|---|
| Time (min) | Biacetyl (wppm)* |
| 0 | 82.8 |
| 5 | 71 |
| 60 | 38 |
| 1100 | <1 |

*Detection limit of 1 wppm.

Example 1

Biacetyl Removal from DMMA Containing 3299 WPPM Methacrylic Acid

Stock solution C, consisting of 100 wppm biacetyl in uninhibited, MAA-free DMMA, was prepared and the concentration verified by GC using the instrument and methodology described above. Stock solution D, consisting of 1210 wppm oPD in uninhibited, MAA-free DMMA, also was prepared. Stock Solution D and methacrylic acid were added concurrently to Stock Solution C, such that the oPD concentration was 264 wppm, the biacetyl concentration was 78.2 wppm, the methacrylic acid concentration was 3300 wppm, and the oPD:biacetyl mole ratio was 2.46. After stirring for 5 minutes in a closed system at ambient temperature, the biacetyl concentration was below the GC detection limit. This biacetyl concentration did not change significantly after stirring overnight. All data can be seen in Table 2 below.

TABLE 2

Biacetyl Removal from DMMA Containing 3299 WPPM Methacrylic Acid

| Time (min) | Biacetyl (wppm)* |
|---|---|
| 0 | 78.2 |
| 5 | <1 |
| 60 | <1 |
| 1100 | <1 |

*Detection limit of 1 wppm.

Example 2

Biacetyl Removal from Stripped Crude MMA (SCMMA) Containing 5000 WPPM Methacrylic Acid Stripped crude MMA (SCMMA, derived from an ACH-based process), which typically contains 5000 wppm MAA, was spiked with biacetyl to 85 wppm and the concentration verified by GC. To this solution was added solid oPD such that the oPD concentration was 203 wppm and the oPD:biacetyl ratio was 1.9. After stirring for 5 minutes in a closed system at ambient temperature, the biacetyl concentration was determined to be 1.3 wppm by GC. This biacetyl concentration did not change significantly after stirring overnight. Data can be seen in Table 3.

TABLE 3

Biacetyl Removal from SCMMA Containing ~5000 WPPM Methacrylic Acid

| Time (min) | Biacetyl (wppm) |
|---|---|
| 0 | 85 |
| 5 | 1.3 |
| 60 | 1.1 |
| 1100 | 1.0 |

We claim:
1. A process for removing biacetyl from an alpha-, beta-unsaturated carboxylic acid ester, comprising:
  a) treating a crude alpha-, beta-unsaturated carboxylic acid ester to produce said alpha-, beta-unsaturated carboxylic acid ester which comprises biacetyl and has a weak acid content of between 0.001% and 5.0% by weight, based on the total weight of said alpha-, beta-unsaturated carboxylic acid ester; wherein the weak acid comprises carboxylic acid selected from the group consisting of acrylic acid and methacrylic acid, and
  b) adding to said alpha-, beta-unsaturated carboxylic acid ester, at a temperature of from 40 to 120° C., from 1 to 10 molar ratio of an aromatic ortho-diamine, based upon moles of biacetyl, to produce an amine-treated ester mixture, said aromatic ortho-diamine having the formula:

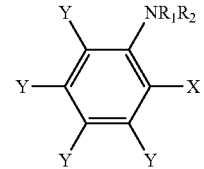

where X is $NR_3R_4$ and
  $R_1$, $R_2$, $R_3$, $R_4$, and Y are independently selected from hydrogen, alkyl, phenyl, and naphthyl.
2. The process according to claim 1 wherein said treating step a) is accomplished by performing one or more purification or separation steps.
3. The process according to claim 2, wherein the weak acid comprises methacrylic acid, and said treating step a) comprises adding a quantity of weak acid to said alpha-, beta-unsaturated carboxylic acid ester sufficient to bring said methacrylic acid content to between 0.001% and 5.0% by weight.
4. The process according to claim 3, wherein the weak acid content of said alpha-, beta-unsaturated carboxylic acid ester is between 0.005% and 1% by weight, based on the total weight of said alpha-, beta-unsaturated carboxylic acid ester.
5. The process according to claim 4, wherein the weak acid content of said alpha-, beta-unsaturated carboxylic acid ester is between 0.3% and 0.5% by weight, based on the total weight of said alpha-, beta-unsaturated carboxylic acid ester.
6. The process according to claim 1, wherein said aromatic ortho-diamine is ortho-phenylenediamine.
7. The process according to claim 6, further comprising separating a diamine-biacetyl adduct and excess ortho-phenylenediamine from said amine-treated ester mixture to produce a purified alpha-, beta-unsaturated carboxylic acid ester.
8. The process according to claim 1, wherein said crude alpha-, beta-unsaturated carboxylic acid ester is the product of a $C_3$-$C_{10}$ alpha-, beta-unsaturated carboxylic acid reacted with a $C_1$-$C_{10}$ alcohol or methacrylamide esterified with a $C_1$-$C_{10}$ alcohol.
9. The process according to claim 1, wherein the temperature is from 60 to 90° C.

* * * * *